(12) United States Patent
Taal et al.

(10) Patent No.: US 7,875,298 B2
(45) Date of Patent: Jan. 25, 2011

(54) BOTANICAL EXTRACT COMPOSITION

(76) Inventors: Leendert Taal, Loakendiek 2, 7255 NL Hengelo (NL); Anita Monique Taal-Vlas, Loakendiek 2, 7255 NL Hengelo (NL)

( * ) Notice: Subject to any disclaimer, the term of this patent is extended or adjusted under 35 U.S.C. 154(b) by 490 days.

(21) Appl. No.: 10/585,662

(22) PCT Filed: Jan. 7, 2005

(86) PCT No.: PCT/EP2005/000191

§ 371 (c)(1),
(2), (4) Date: Feb. 6, 2008

(87) PCT Pub. No.: WO2005/067951

PCT Pub. Date: Jul. 28, 2005

(65) Prior Publication Data

US 2008/0255225 A1    Oct. 16, 2008

(30) Foreign Application Priority Data

Jan. 7, 2004   (EP) ................................. 04075001

(51) Int. Cl.
A61K 36/254 (2006.01)
A61K 36/236 (2006.01)
A61K 36/00 (2006.01)
A61K 36/48 (2006.01)
A61K 36/67 (2006.01)
A61K 36/899 (2006.01)

(52) U.S. Cl. ..................... 424/725; 424/757; 424/734; 424/773; 424/774; 424/750

(58) Field of Classification Search ...................... None
See application file for complete search history.

(56) References Cited

U.S. PATENT DOCUMENTS

| 6,579,543 B1 * | 6/2003 | McClung ..................... 424/728 |
| 7,087,250 B2 * | 8/2006 | Marchioni .................. 424/618 |
| 2002/0192241 A1 | 12/2002 | Chen et al. |

FOREIGN PATENT DOCUMENTS

| DE | 19853919 | 5/2000 |
| EP | 0270690 | 6/1987 |
| WO | WO 01/34170 A2 * | 5/2001 |
| WO | 02/47701 | 6/2002 |

OTHER PUBLICATIONS

Flynn, The herbal management of stress, Austrilian journal of medical herbalism, 1996: 8 (1): 15-18.*
Widy-Tyszkiewicz et al, A randomized double blind study of sedative effects of phytotherapeutic containing valerian, hops, balm and motherwort versus placebo, Herba polonica, (1997) vol. 43, No. 2, pp. 154-159.*
Singh et al, Therapeutic potential of Kava in the treatment of anxiety disorders, CNS drugs 2002: 16 (11): 731-743.*
Sandoval, Cat's claw (Uncaria tomentosa) protects against oxidative stress and indomethacin-induced intestinal inflammation, Gastroenterology, 1997; 112 (4 suppl.): A1081.*
Disorders from Merck manual, pp. 1-24, accessed on Feb. 17, 2009.*
Dementia from Merck manual, pp. 1-3, accessed on Feb. 17, 2009.*
Alzheimer's disease from Merck manual, pp. 1-21, accessed on Feb. 17, 2009.*
Walker, Personality, coping and sex as psychosocial aspects of psoriatic arthropathy, Dermatology and Psychosomatics, (2003) vol. 4, No. 1, pp. 27-32.*
Yu et al, Effects of long-term oral administration of polymeric microcapsules containing tyrosinase on maintaining decreased systemic tyrosine levels in rats, Journal of pharmaceutical sciences, (Apr. 2004) vol. 93, No. 4, pp. 831-837.*
Cleaver, Defective repair replication of DNA in xeroderma pigmentosum, NATURE [London], (1968) vol. 218, No. 5142, pp. 652-656.*
Jullien, A new treatment for psoriasis, Nouvelles Dermatologiques, (Apr. 2006) vol. 25, No. 4, pp. 264-272.*

(Continued)

*Primary Examiner*—Qiuwen Mi
(74) *Attorney, Agent, or Firm*—Harness, Dickey & Pierce, P.L.C.

(57) ABSTRACT

A kit including a first composition comprising leaves of *Melissa officinalis*, or parts thereof; a second composition comprising *Eleutherococcus senticosus*, or parts thereof; a third composition comprising *Avena sativa*, or parts thereof; a fourth composition comprising *Ballota nigra*, or parts thereof; a third composition comprising the roots of *Glycyrrhiza glabra*/gan cao, or parts thereof; and a sixth composition comprising roots of *Uncaria tomentosa*, or parts thereof. The invention further relates to a kit for use as a medicament, to a kit for use in the treatment of disorders in mammals, like humans, horses, cows, pigs and pets, to a kit for use in the treatment of lupus, multiple sclerosis, rheumatoid arthritis, rheumatism, osteoporosis, asthma in humans or tale and mane eczema in horses, and to the use of the kit for the treatment of lupus, multiple sclerosis, rheumatoid arthritis, rheumatism, osteoporosis, asthma in humans or tale and mane eczema in horses.

4 Claims, No Drawings

OTHER PUBLICATIONS

Freshney, Culture of Animal Cells, A Manual of Basic Technique, Alan R. Liss, Inc., 1983, New York, p. 4.*

Steinman et al, How to successfully apply animal studies in experimental allergic encephalomyelitis to research on multiple sclerosis, Ann Neurol 2006; 60: 12-21.*

Sriram et al, Experimental allergic encephalomyeliits: a misleading model of multiple sclerosis, Ann Neurol 2005; 58: 939-945.*

Multiple Sclerosis from Merck Manual, accessed on Jul. 15, 2010, pp. 1-6.*

Lublin et al, Defining the clinical course of multiple sclerosis: results of an international survey. National Multiple Sclerosis Society (USA) Advisory Committee on Clinical Trials of New Agents in Multiple Sclerosis, Neurology. 1996 46(4): 907-11.*

Peizhong et al, Is multiple sclerosis a mitochondrial disease? Biochimica et biophysica acta, (Jan. 2010) vol. 1802, No. 1, pp. 66-79.*

Hans-Peter, High-dose, high-frequency recombinant interferon beta-1a in the treatment of multiple sclerosis, Expert opinion on pharmacotherapy, (Feb. 2009) vol. 10, No. 2, pp. 291-309.*

Fiske et al, Multiple sclerosis and oral care, Dental update, (Jul.-Aug. 2002) vol. 29, No. 6, pp. 273-283.*

Holland et al, Adherence to disease-modifying therapy in multiple sclerosis: Part II, Rehabilitation nursing : the official journal of the Association of Rehabilitation Nurses, (Nov.-Dec. 2001) vol. 26, No. 6, pp. 221-226.*

"Randomized Double Blind Trial of an Extract from the Pentacyclic Alkaloid-Chemotype of Uncaria Tomentosa for the Treatment of Rheumatoid Arhtritis". Mur Erich et al. The Journal of Rheumatology, vol. 29, No. 4, pp. 678-681, Apr. 2002.

Database WPI. Section Ch, Week 200262, Derwent Publications Ltd., London, GB, Class B04, AN 2002-581546 XP002305247 & RU 2185182 C2 (Khvostenkov S I) Jul. 20, 2002.

International Search Report (PCT/ISA/210).

* cited by examiner

BOTANICAL EXTRACT COMPOSITION

The present invention relates to a kit comprising six botanic compositions. The invention further relates to a kit for use as a medicament, to a kit for use in the treatment of disorders in mammals, like humans, horses, cows, pigs and pets, to a kit for use in the treatment of lupus, multiple sclerosis, rheumatoid arthritis, rheumatism, osteoporosis, asthma in humans or tale and mane eczema in horses, and to the use of the kit for the treatment of lupus, multiple sclerosis, rheumatoid arthritis, rheumatism, osteoporosis, asthma in humans or tale and mane eczema in horses Lupus and tale and-mane eczema are diseases which are characterized by a complete derangement of the metabolism in a human or horse, respectively. Lupus is a general name for several auto-immune diseases such as lupus erythematosus, lupus verucosus, lupus vulgaris, psoreasis and eczema. Tale and mane eczema, also known as summer-itching or sweet-itching, is a disease that is common under horses.

It is believed that the complete derangement of the metabolism in the human or horse results in an accumulation of homotoxins in the connective tissues located in the skin of humans or in the tale region or mane region of horses. However, it may also manifest itself in other parts of the body, such as internal organs.

The skin of human patients suffering from lupus is often very sensitive to light. In severe cases direct light exposure should be avoided, ultimately leading to a social isolation of the patient. Further, it is known that patients suffering from lupus may have a poorly working liver or kidney due to progressive attacks of inflammation.

Horses suffering from tale and mane eczema feel a constant itching in the affected places. To alleviate this itching, horses scratch their affected places on rough surfaces. however, this scratching leads to severe inflammation of the affected places and ultimately the horses are no longer capable of functioning normally.

Although, lupus and tale and mane eczema are diseases which are known for many years, a truly effective cure has not yet been found. Treatments used at present focus on symptoms, i.e. inflammation, but do not treat the disease itself.

The objective of the present invention is to provide for a medicament which is truly effective for use in the treatment of lupus and tale and mane eczema.

A first aspect of the present invention relates to a kit comprising:
- a first composition comprising leaves of *Melissa Officinalis*, or parts thereof;
- a second composition comprising *Eleutherococcus Senticosus*, or parts thereof;
- a third composition comprising *Avena sativa*, or parts thereof;
- a fourth composition comprising *Ballota Nigra*, or parts thereof;
- a fifth composition comprising roots of *Glycyrrhiza glabra*/gan cao, or parts thereof; and
- a sixth composition comprising roots of *Uncaria Tomentosa*, or parts thereof.

One of the pharmaceutically active compounds in the leaves of *Melissa Officinalis* is rose mary acid. Further, the pharmaceutically active compounds of *Eleutherococcus senticosus* are believed to be present in the polyphenol-fraction. Moreover, one of the pharmaceutically active compounds in parts of *Bollota Nigra* is caffeic acid. Further, the pharmaceutically active compounds of the roots of *Glycyrrhiza glabra*/gan cao are believed to be present in the saponin-fraction and the pharmaceutically active compounds of the roots of *Uncaria Tomentosa* are believed to be present in the alkaloid-fraction.

The above mentioned kit of compositions is especially suited for the treatment of human patients suffering from lupus and horses suffering from tale and mane eczema, although other mammals may also be treated with it. By administering the compositions of the kit to patients, the system-reticulo-endothelial blockade is lifted and the biofeedback restored. This leads to an improvement of the overall physical condition of the patient. It is believed that due to the improvement of the physical condition of the patient, the homotoxins which are present in connective tissue of the body are broken down. This stops the accumulation of homotoxins in the connective tissue, resulting in a halt to the inflammation of the skin and other organs. Due to the overall improvement of the physical condition of patients, the above mentioned kit can also be beneficial for human patients suffering from other diseases than lupus, such as for example multiple sclerosis, rheumatoid arthritis, rheumatism, osteoporosis and asthma.

In a preferred embodiment of the kit,
- the first composition comprises a unit dose of 100-1000 mg of leaves of *Melissa Officinalis*, or parts thereof;
- the second composition comprises a unit dose of 100-1000 mg of *Eleutherococcus senticosus*, or parts thereof;
- the third composition comprises a unit dose of 100-1000 mg of *Avena sativa*, or parts thereof;
- the fourth composition comprises a unit dose of 100-1000 mg *Ballota Nigra*, or parts thereof;
- the fifth composition comprises a unit dose of 100-1000 mg of the roots of *Glycyrrhiza glabra*/gan cao, or parts thereof;
- the sixth composition comprises a unit dose of 100-1000 mg of the roots of *Uncaria Tomentosa*, or parts thereof.

A second aspect of the present invention relates to a kit comprising:
- a first composition comprising leaves of *Melissa Officinalis*, or parts thereof;
- a second composition comprising *Eleutherococcus Senticosus*, or parts thereof;
- a third composition comprising *Avena sativa*, or parts thereof;
- a fourth composition comprising roots of *Piper Methysticum*, or parts thereof;
- a fifth composition comprising roots of *Glycyrrhiza glabra*/gan cao, or parts thereof;
- a sixth composition comprising roots of *Uncaria Tomentosa*, or parts thereof.

One of the pharmaceutically active compounds in the leaves of Melissa Officinalis is rose mary acid. Further, the pharmaceutically active compounds of *Eleutherococcus senticosus* are believed to be present in the polyphenol-fraction. Moreover, one of the most important pharmaceutically active compounds in the roots of *Piper methysticum* is most likely resine. Further, it is believed that the pharmaceutically active compounds of the roots of *Glycyrrhiza glabra*/gan cao are present in the saponin-fraction and that the pharmaceutically active compounds of the roots *Uncaria Tomentosa* are present in the alkaloid-fraction.

The above mentioned kit is especially suited for the treatment of horses, however other mammals may also be treated with it. It is believed that administering the compositions of the kit lifts the system-reticulo-endothelial blockade and restores the biofeedback. This leads to an improvement of the overall physical condition of the horse. Due to the improvement of its physical condition, the homotoxins that cause the itching are broken down. This prevents the homo-toxins from accumulating in the connective tissue of the tale and mane region, resulting in less or no itching.

In a preferred embodiment of the kit of the present invention;

the first composition comprises a unit dose of 100-1000 mg leaves of *Melissa Officinalis*, or parts thereof;

the second composition comprises a unit dose of 100-1000 mg of *Eleutherococcus senticosus*, or parts thereof;

the third composition comprises a unit dose of 100-1000 mg of *Avena sativa*, or parts thereof;

the fourth composition comprises a unit dose of 100-1000 mg roots of *Piper methysticum*, or parts thereof;

the fifth composition comprises a unit dose of 100-1000 mg roots of *Glycyrrhiza glabra*/gan cao, or parts thereof.

the sixth composition comprises a unit dose of 100-1000 mg roots of *Uncaria Tomentosa*, or parts thereof.

In a preferred embodiment of the above mentioned kits, a composition comprises a pharmaceutically acceptable carrier.

Moreover, it is preferred if a composition is in the form of a capsule or tablet, although a liquid or sachet may also be used.

A third aspect of the present invention relates to a kit as described above for use as a medicament.

A fourth aspect of the present invention relates to a kit as described above for use in the treatment of disorders in mammals, like humans, horses, cows, pigs and pets.

A fifth aspect of the present invention relates to a kit as described above for use in the treatment of lupus, multiple sclerosis, rheumatoid arthritis, rheumatism, osteoporosis, asthma in humans or tale and mane eczema in horses.

A last aspect of the present invention relates to the use of a kit as described above in the treatment of lupus, multiple sclerosis, rheumatoid arthritis, rheumatism, osteoporosis, asthma in humans or tale and mane eczema in horses.

The invention will be described by the following examples. These examples are given for illustration purposes and are not intended to limit the scope of the invention.

EXAMPLES

Example 1

A Spanish female patient suffering from lupus erythematosus was treated with the compositions of the kit of the present invention. Before treatment the patient had a poor working liver and was very sensitive to light. Exposure to light caused several inflammatory places on the skin. During 5 months the patient was treated with the compositions of the kit of the invention. She was administered:

three times a day two capsules containing 210 mg of leaves of *Melissa Officinalis;* three times a day two capsules containing 250 mg of *Eleutherococcus senticosus;* three times a day two capsules containing 250 mg of *Avena sativa.* three times a day one capsule containing 150 mg of an extract of *Ballota nigra;* three times a day two capsules containing 250 mg parts of the roots of *Glycyrrhiza glabra*/gan cao; and three times a day one capsule containing 350 mg parts of roots of *Uncaria Tomentosa.*

After 6 months the patient was exposed to day-light and no inflammation of the skin took place. Further, MRI-pictures were taken form the liver and they showed that the dark spots, indicating a poorly working liver, had disappeared.

Example 2

A group of 102 horses (98 Fjords, 2 Icelanders and 2 Half lings) suffering from tale and mane eczema were treated with the compositions of the kit of the present invention. Before treatment the horses had several infections in the tale and mane region. During a period varying from 1 to 6 months the horses were administered:

three times a day two capsules containing 210 mg of leaves of *Melissa Officinalis;* three times a day two capsules containing 250 mg of *Eleutherococcus senticosus;* three times a day two capsules containing 250 mg of *Avena sativa;* three times a day two capsules containing 300 mg parts of the roots of *Piper methysticum;* three times a day two capsules containing 250 mg parts of the roots of *Glycyrrhiza glabra*/gan cao;

three times a day one capsule containing 350 mg parts of the roots of *Uncaria Tomentosa.*

Within a period of six months the conditions of all the horses were evaluated. Seventy nine horses did no longer suffer from tale and mane eczema. Twelve horses showed improvement, although the tale and mane eczema was not cured completely. Eleven horses showed no improvement. It is believed that the disease has affect these eleven horses beyond a biological border, making treatment fruitless.

The invention claimed is:

1. A kit comprising:
a first composition including a unit dose of 100-1000 mg parts of *Melissa officinalis;*
a second composition including a unit dose of 100-1000 mg parts of *Eleutherococcus senticosus;*
a third composition including a unit dose of 100-1000 mg parts of *Avena sativa;*
a fourth composition including a unit dose of 100-1000 mg parts of *Ballota nigra,*
a fifth composition including a unit dose of 100-1000 mg roots of *Glycyrrhiza Glabra*; and
a sixth composition including a unit dose of 100-1000 mg roots of *Uncaria tomentosa.*

2. A kit comprising:
a first composition including a unit dose of 100-1000 mg parts of *Melissa officinalis;*
a second composition including a unit dose of 100-1000 mg parts of *Eleutherococcus senticosus;*
a third composition including a unit dose of 100-1000 mg parts of *Avena sativa;*
a fourth composition including a unit dose of 100-1000 mg roots of *Piper methysticum;*
a fifth composition including a unit dose of 100-1000 mg roots of *Glycyrrhiza Glabra*; and
a sixth composition including a unit dose of 100-1000 mg roots of *Uncaria tomentosa.*

3. The kit according to claim 1, wherein at least one of the compositions includes a pharmaceutically acceptable carrier.

4. The kit according to claim 1, wherein at least one of the compositions is in the form of a capsule or tablet.

* * * * *